United States Patent
White

(10) Patent No.: US 6,589,521 B1
(45) Date of Patent: Jul. 8, 2003

(54) SEX ATTRACTANT AND MATING DISRUPTANT FOR THE OMNIVEROUS LEAFROLLER AND ORANGE TORTRIX MOTH

(75) Inventor: Jeffrey White, Billings, MT (US)

(73) Assignee: Scentry Biologicals, Inc., Billings, MT (US)

( * ) Notice: Subject to any disclaimer, the term of this patent is extended or adjusted under 35 U.S.C. 154(b) by 0 days.

(21) Appl. No.: 09/587,487

(22) Filed: Jun. 5, 2000

(51) Int. Cl.$^7$ ................... A01N 37/06; A01N 35/02
(52) U.S. Cl. ................ 424/84; 514/546; 514/549; 514/552; 514/703
(58) Field of Search ................ 424/84; 514/546, 514/703, 549, 552

(56) References Cited

U.S. PATENT DOCUMENTS

| | | |
|---|---|---|
| 3,980,771 A | 9/1976 | Meijer et al. |
| 4,059,689 A | 11/1977 | Struble et al. |
| 4,147,771 A | 4/1979 | Struble et al. |
| 4,323,556 A | 4/1982 | Dal Moro et al. |
| 4,325,941 A | 4/1982 | Dal Moro et al. |
| 4,487,759 A | 12/1984 | Nesbitt et al. |
| 5,236,715 A | 8/1993 | McDonough et al. |
| 5,380,524 A | 1/1995 | McDonough et al. |
| 5,707,638 A | 1/1998 | Losel et al. |
| 5,725,849 A | 3/1998 | Mochizuki et al. |
| 5,728,376 A | 3/1998 | Attygalle et al. |

OTHER PUBLICATIONS

Chemical Abstracts 83: 144741, 1975.*
Ando, T. et al., "Two–component Sex Attractants for male moths of the subfamily Tortricinae( Lepidoptera)," Agric. Biol. Chem., vol. 42(5), pp. 1081–1083, 1978.*
Chemical Abstracts 89: 56768 (1978).*
Hill, A.S. et al., "Sex pheromone of the orange tortrix moth, Argyrotaenia citrana (Lepidoptera Tortricidae)," J. Chem. Ecol., 1975, vol. 1, No. 2, pp. 215–224.*

* cited by examiner

Primary Examiner—John Pak
(74) Attorney, Agent, or Firm—Charles F. Meroni, Jr.; Meroni & Meroni, P.C.; Kalim S. Fuzail

(57) ABSTRACT

A composition of (Z)-11-tetradecenyl acetate and (Z)-11-tetradecenal in a weight ratio of about 50:50 to about 90:10 is a highly effective mating disruptant for the male Orange Tortrix and Omniverous Leafroller moths. In a preferred embodiment, the weight ratio of (Z)-11-tetradecenyl acetate and (Z)-11-tetradecenal is about 75:25. The composition demonstrates biological activity in the form of enhanced mating disruption efficacy that is greater than any discovery or development to date for the Orange Tortrix of the Omniverous Leafroller.

2 Claims, No Drawings

SEX ATTRACTANT AND MATING DISRUPTANT FOR THE OMNIVEROUS LEAFROLLER AND ORANGE TORTRIX MOTH

FIELD OF THE INVENTION

The invention relates to a novel composition and use thereof for insect control. More particularly, the invention relates to a mating disruption composition comprising (Z)-11-tetradecenyl acetate and (Z)-11-tetradecenal in a weight ratio of about 50:50 to about 90:10, and more preferably in a weight ratio of about 75:25 respectively, and method of use of the composition as a mating disruptant for both the Omniverous Leafroller and Orange Tortrix moth.

DESCRIPTION OF THE PRIOR ART

The Omniverous Leafroller (OLR) moth, scientific name *Platynota stultana*. Walsingham, produces five to six generations a year and is a major pest of grapes. OLR larvae can directly reduce grape yields by causing injury to the flowers or the developing berries. Author(s), Grape Pest Management, Vol. Number, p. 126 (month, year). Larvae cause damage to grape clusters by creating injuries that create avenues for infection by bunch rot organisms such as fungus or bacteria. As the berries ripen, the rotting and fermenting fruit attract secondary pests such as the raisen moth, Drosophila flies, and dried fruit beetles that further exacerbate the situation. Id. The OLR moth also attacks cotton, alfalfa, celery, lettuce, tomatoes, red peppers, sugar beets, citrus, roses, carnations, chrysanthemums, asters and over thirty-five other crops.

The Orange Tortrix (OT) moth, scientific name *Argyrotaenia citrana* Fernald, causes the same kind of damage as the OLR moth in inland areas. Overwintering OT larvae feed on any soft, exposed vine tissue, weeds, and in grapes that have mummified on the vine. Spring feeding is on buds, canes, and webbed leaves. Larvae then enter the bunches and make nests of webbing among the berries. Besides injury to leaves and berry stems, their feeding on berries allows entry of bunch rot disease organisms.

Various strategies have been recommended to combat the menace of these pests. At the present time OT and OLR moth infestations are controlled by the application of a variety of insecticides, larvalcides, and Bacillus thurengiensis variants. These techniques are utilized with the intention of killing the moths at one or another of their growth stages.

Heavy dependence on pesticides, however, has created many problems such as environmental pollution, pesticide resistance and human health problems. Most alternatives to chemical pest control have some other limitations. For example, complexes of parasites and predators give appreciable biological control of some pests in unsprayed orchards. In commercial orchards, however, the control by these biological agents may not be sufficient to provide effective population suppression.

Consequently, insecticide applications are applied to reduce the infestations and protect the fruit. Repeated applications of insecticides to control pests may not be cost efficient in the long run. The natural balance of pest and predator may be upset in the orchard ecosystem, reducing the populations of natural enemies, and triggering the population build up of secondary pests. An environmentally friendly approach such as pheromone mating disruption could afford sufficient control of orchard pests while conserving natural enemies.

Mating disruption involves the use of pheromones. Pheromones are released by one member of a species to cause a specific interaction with another member of the same species. Pheromones may be further classified on the basis of the interaction mediated, such as alarm, aggregation or sex pheromone. It is the sex pheromone of insects that are of particular interest to agricultural pest management practitioners and applies to this case. Mating disruption is based on the principle that when the sex pheromone is released in the air in an orchard in sufficiently high quantities, the males are unable to orient to natural sources of sex pheromone (females) and fail to locate the calling female and insemination reproduction is prevented.

Various non-lethal pheromone mating disruption techniques have been developed for the OLR and OT moths. These pheromone applications have proven successful on the majority of the orchards to which they have been applied. For example, the University of California, Davis found that most of the disruptive activity of the OLR moth was provided by the components that are found in greatest amounts in living female OLR moths, the components being (E)-11-tetradecenyl acetate and (Z)-11-tetradecenyl acetate. (E)-11-tetradecenyl acetate and (Z)-11-tetradecenyl acetate combined in a 9:1 ratio disrupted pheromone communication more effectively than did either component alone. Shorey, Sick, and Gerber, Journal of Physiological and Chemical Ecology, p. 1270–1274 (October 1995).

What has not been developed, however, is one single pheromone blend effective in disrupting both the OLR and OT moths together. This is of particular significance since the OLR and OT moths are usually both present in the same location due to similar feeding habits.

Therefore, it is an object of the invention to provide a pest control composition that will reduce the use of a broad spectrum of chemical pesticides which are widely used in orchard pest management.

Another object of the invention is to provide a pest control composition that can be used with other biological controls without adverse effects.

Yet another object of the invention is to provide a pest control composition that is not harmful to farm workers.

Still another object of the invention is to provide a pest control composition that will not leave a toxic residue on fruits.

Other objects and advantages of the invention will become readily apparent from the ensuing description.

SUMMARY OF THE INVENTION

What has been discovered is a two component pheromone system by itself or in conjunction with other components that is significantly more effective at disrupting the mating of the OLR moth than existing pheromone formulations. Additionally, what has been discovered is that the same two component system of the present invention is also a superior mating disrupter of the OT moth.

It has been discovered that a composition of two compounds, namely, (Z)-11-tetradecenyl acetate and (Z)-11-tetradecenal, in a weight ratio of about 50:50 to about 90:10, and more preferably in a weight ratio of about 75:25 respectively, is a highly effective mating disruptant for the male species of both the OT and OLR moths. The composition demonstrates biological activity towards both the OT and OLR males comparable to or greater than that of the females of either species.

DETAILED DESCRIPTION OF THE PREFERRED EMBODIMENTS

The mating disruptant composition of the invention requires the presence of two compounds, (Z)-11-tetradecenyl acetate (hereinafter I) and (Z)-11-tetradecenal (hereinafter II), in the mixture. The weight ratio of the compounds in the composition that is an effective mating disruptant for both the OLR and OT moths is about 50:50 to about 90:10 (I:II). The preferred weight ratio of the pheromone composition being about 75:25 (I:II). The composition may be dispensed alone or in combination with a carrier. The carrier may be an inert liquid or solid. Examples of suitable carriers are vegetable oils, refined mineral oils, rubbers, plastics, silica, diatomaceous earth, and cellulose powder. With these carriers, the dispensers can be loaded with larger amounts of the pheromone composition giving longer dispenser life without serious suppression of disruption.

It is contemplated that the pheromone composition of the present invention may also be used as a detecting agent, monitoring agent, or control agent for the OLR and OT moths. The pheromone composition may be used as trap bait or may otherwise be applied to a locus of the moths, that is, an area where the moths are present or where they may occur. The trap or lure may then be placed on or within close proximity to a tree or vine, that is, within 20 feet.

The composition of the present invention is used in an amount effective to induce the desired male response. In the case of an attractant response, for example, an effective amount is defined as that quantity of the composition that attracts OLR and OT male moths to the location of a bait at a rate significantly higher than males are attracted to a location that is not baited.

Factors such as population density, temperature, wind velocity, and rain will influence the response of the moths and thus the actual number of moths attracted to a bait or trap. The amount of composition in a particular set of circumstances that will be within an effective range can be readily determined by dose response field tests.

In the case where the desired response is disruption of mating by confusing or inhibiting the male moth, an effective amount is defined as that quantity of the composition which permeates the atmosphere such that males are prevented from orienting to and inseminating the females, i.e., disruption of mating, at a rate significantly higher than disruption of mating of males at an untreated location. As with the attractant response, factors such as population density, temperature, wind velocity, and rain will influence the actual number of moths disrupted. The exact dose to use in any particular set of circumstances can readily be determined by dose response field testing.

It is envisioned that the pheromone composition would be useful in disrupting the mating of the OLR and OT moths when used in conjunction with a dispenser or pheromone disseminator (controlled release substrate) known in the art. The evaporation rate of the pheromone composition is controlled by using a controlled release substrate (CRS). Preferred CRS are a polyvinyl chloride (PVC) matrix containing the pheromone which in turn is covered by a PVC membrane. Typically, the pheromone composition is formulated in PVC or other suitable plastics that may or may not contain inert plasticizers that do not interfere with the activity of the composition. Examples of other CRS are PVC plastic laminates, polyvinyl chloride pellets, microcapillaries, PVC spirals or microencapsulated formulations.

It is also contemplated that the pheromone blend may be used as a detector or monitoring agent by utilizing the blend in a lure designed for insect trapping. Traps may be baited with the novel composition of the invention and the catch tabulated to determine size and location of an infestation. Economic use of appropriate pest management systems can be determined in this manner.

Other contemplated uses of the composition as a control agent could be carried out in several ways. For example, one method may be to use the compound to attract the insects to suitable substrates and subsequently or simultaneously expose the moths to insecticides which control the moths. An effective amount of the insecticide is used, that is, an amount that is lethal for an exposed insect or at least sublethal but sufficient to incapacitate the insect in regard to mating activity. Insecticides can be used with lures baited with the composition. This eliminates the need to spread the insecticides unnecessarily. It is also envisioned that chemosterilants could also be used in conjunction with the pheromone composition to attract and sterilize male moths.

EXAMPLES

The following examples are intended only to further illustrate the invention and are not intended to limit the scope of the invention which is defined by the claims.

Example 1

100 mg of the pheromone composition was tested on the Omniverous Leafroller (OLR) moth via PVC substrate pheromone spirals to determine the longevity of mating disruption activity on grapes. Various pheromone rates and compositions were applied in a wine vineyard in one acre plots. Applications were made at 130 mating disruption dispensers/spirals per acre in a vineyard with eight feet between vines and twelve feet between rows. Every other vine in every other row was used. Monitoring was accomplished every two weeks using lure baited wing traps that mimicked calling females.

Trap catch is the proxy for mating disruption success. That is to say, if no moths, or even a small number of moths, were caught in traps baited with virgin females or septa lures that approximate virgin females, then the test was proven successful. Meanwhile, a pheromone untreated control was maintained in the same area at the same time for comparison. The catches were statistically compared to determine if there was a significant difference between the pheromone treated and untreated areas.

The following formulations were tested: (a) 88% (Z)-11-tetradecenyl acetate to 12% (Z)-11-tetradecenal; (b) 75% (Z)-11-tetradecenyl acetate to 25% (Z)-11-tetradecenal; (c) 97% (Z)-11-tetradecenyl acetate to 3% (Z)-11-tetradecenal; (d) 75% (Z)-11-tetradecenyl acetate to 25% (Z)-11-tetradecenal in a polyurethane matrix; (e) 90% (E)-11-tetradecenyl acetate to 10% (Z)-11-tetradecenyl acetate, designated as "OLR", and (f) an untreated control. The untreated control measures the true level of moth population and activity in the vineyard. "OLR" refers to the current commercial formula already on the market. The results are indicated below in Table 1.

What is shown in Table 1 is the average trap catches versus time measured in weeks. Two component pheromones are shown as they were used in varying ratios. Standard synthetic lures were placed in the traps to mimic the pheromone calling of a female moth. Under normal circumstances the male moths should have been attracted to the traps. Ideally, if the pheromone composition used for mating disruption is effective, then fewer moths should be able to find the traps. A disrupted plot confuses males to the point that they cannot find a trap or a female. Therefore, the lower the number of moths caught by the synthetic lures in the traps, the more effective the pheromone mating disruption composition.

TABLE 1

Mean number of OLR moths captured in winged traps in grapes using TO pheromone.

| Pheromone Blend | Week 2 | Week 4 | Week 6 | Week 8 | Week 11 | Week 13 | Week 16 | Week 19 |
| --- | --- | --- | --- | --- | --- | --- | --- | --- |
| (a) 88/12 | 0.2 | 0.0 | 0.0 | 0.0 | 0.0 | 0.3 | 0.0 | 0.0 |
| (b) 75/25 | 0.0 | 0.0 | 0.2 | 0.2 | 0.2 | 0.0 | 0.0 | 0.2 |
| (c) 97/3 | 0.0 | 0.2 | 0.5 | 0.0 | 0.3 | 0.0 | 0.0 | 0.2 |
| (d) 75/25 poly | 0.0 | 0.3 | 0.3 | 0.3 | 0.0 | 0.0 | 0.0 | 0.0 |
| (e) OLR | 0.2 | 6.3 | 7.5 | 3.7 | 1.7 | 2.5 | 0.7 | 1.0 |
| (f) Untreated | 2.5 | 12.5 | 28.8 | 11.6 | 15.5 | 20.5 | 5.8 | 26.8 |

As can be seen from Table 1, the 75% (Z)-11-tetradecenyl acetate to 25% (Z)-11-tetradecenal pheromone blend, as well as the other OT blends, is far more efficacious in disrupting mating in the vineyard and confusing the male OLR moths than the currently available commercial formula.

Example 2

The pheromone compositions of Example I were also tested on the Orange Tortrix (OT) moth in the same mariner. The results are indicated below in Table 2.

TABLE 2

Mean number of OT moths captured in winged traps in grapes using TO pheromone.

| Pheromone Blend | Week 2 | Week 4 | Week 6 | Week 8 | Week 11 | Week 13 | Week 16 | Week 19 |
| --- | --- | --- | --- | --- | --- | --- | --- | --- |
| 88/12 | 22.7 | 1.3 | 0.8 | 1.5 | 2.8 | 2.3 | 4.1 | 4.5 |
| 75/25 | 0.0 | 0.2 | 0.5 | 0.5 | 0.2 | 0.2 | 0.3 | 1.2 |
| 97/3 | 0.3 | 0.2 | 0.8 | 0.2 | 0.8 | 0.7 | 1.0 | 2.3 |
| 75/25 poly | 0.0 | 0.0 | 0.3 | 0.3 | 0.0 | 0.0 | 0.2 | 0.8 |
| OLR | 9.8 | 40.0 | 79.5 | 29.5 | 30.7 | 19.3 | 17.3 | 38.0 |
| Untreated | 35.3 | 37.8 | 114.2 | 35.3 | 58.3 | 41.5 | 24.2 | 67.3 |

As can be seen from Table 2, the 75% (Z)-11-tetradecenyl acetate to 25% (Z)-11-tetradecenal pheromone blend is far more efficacious in disrupting mating in the vineyard and confusing the male OT moths than any of the other pheromone compositions.

Thus, the 75% (Z)-11-tetradecenyl acetate to 25% (Z)-11-tetradecenal ratio disrupts OT better than any other ratio of same, and also disrupts OLR better than the currently used OLR commercial formula.

It is to be understood that the foregoing detailed description is given merely by way of illustration and that modification and variations may be made within without departing from the spirit and scope of the invention.

I claim:

1. A method of disruption of mating of OLR moths, which comprises applying to the locus of male OLR moths an effective disruptant amount of a composition which comprises a mixture of (Z)-11-tetradecenyl acetate and (Z)-11-tetradecenal in a weight ratio of about 50:50 to about 90:10.

2. A method of disruption of mating of OLR moths, which comprises applying to the locus of male OLR moths an effective disruptant amount of a composition which comprises a mixture of (Z)-11-tetradecenyl acetate and (Z)-11-tetradecenal in a weight ratio of about to about 75:25.

* * * * *